United States Patent [19]
Kroll

[11] Patent Number: 5,925,068
[45] Date of Patent: Jul. 20, 1999

[54] METHOD FOR DETERMINING AN ICD REPLACMENT TIME

[75] Inventor: Mark W. Kroll, Simi Valley, Calif.

[73] Assignee: Pacesetter, Inc., Sylmar, Calif.

[21] Appl. No.: 09/019,664

[22] Filed: Feb. 6, 1998

Related U.S. Application Data

[62] Division of application No. 08/784,566, Jan. 21, 1997, Pat. No. 5,741,307.

[51] Int. Cl.$^6$ ..................................................... A61N 1/362
[52] U.S. Cl. ................................................................ 607/29
[58] Field of Search ............................... 607/29, 5, 9, 27, 607/28

[56] References Cited

U.S. PATENT DOCUMENTS

| | | |
|---|---|---|
| 4,295,474 | 10/1981 | Fischell . |
| 4,345,603 | 8/1982 | Schulman . |
| 4,606,350 | 8/1986 | Frost ........................................... 607/29 |
| 4,809,697 | 3/1989 | Causey et al. . |
| 4,944,299 | 7/1990 | Sergiu . |
| 5,137,021 | 8/1992 | Wayne et al. ............................... 607/29 |
| 5,312,444 | 5/1994 | Bocek et al. . |
| 5,370,668 | 12/1994 | Shelton et al. . |
| 5,458,624 | 10/1995 | Renirie et al. .............................. 607/29 |

*Primary Examiner*—Scott M. Getzow

[57] ABSTRACT

Improved methods of determining the recommended replacement time (RRT), and therefore extending the longevity, of implantable electronic medical devices, especially implantable cardioverter-defibrillators, pacemakers and similar devices which rely on a battery having at least a minimal charge in order for the device to perform its intended function and devices employing these methods are described. In one embodiment the improved method entails independent measurement of at least two different indicators of battery strength, at least one of which is affected by the battery's internal impedance. In a preferred embodiment, terminal battery voltage and capacitor charge time are independently monitored. If the terminal battery voltage falls below a predetermined minimum threshold or the capacitor charge time is confirmed to exceed a predetermined maximum charge time, an RRT signal is issued. In an alternative embodiment, an RRT signal is also issued by the medical device when one indicator of battery strength, for example, battery terminal voltage, falls below a predetermined intermediate voltage but is above the minimum threshold voltage and a second indicator of battery strength, for example, capacitor charge time, exceeds its predetermined maximum threshold.

15 Claims, 3 Drawing Sheets

METHOD FOR DETERMINING AN ICD REPLACMENT TIME

This application is a divisional of application Ser. No. 08/784,566, filed on Jan. 21, 1997, now U.S. Pat. No. 5,741,307.

FIELD OF THE INVENTION

The subject matter disclosed and claimed herein relates to improved implantable medical devices and methods. In particular, improved methods of determining the recommended replacement time (RRT) of implantable electronic medical devices, especially implantable cardioverter-defibrillators, pacemakers and similar devices which rely on a battery having at least a minimal charge in order for the device to perform its intended function.

BACKGROUND OF THE INVENTION

Implantable electronic medical devices serve many functions. A common function is to provide electrical stimulation to a particular muscle or organ of the body and/or to monitor the body's own natural electrical stimulation of that particular region. For example, an electronic pacemaker functions to provide electrical stimulation pulses, at a controlled rate, to selected chambers of the heart in order to ensure that the heart beats. Similarly, an implantable cardioverter-defibrillator (ICD) provides electrical stimulation pulses to selected chambers of the heart. The stimulation pulses from an ICD are much stronger and less frequent than those produced by pacemakers and are intended to correct rapid, uncoordinated heart beats (fibrillation).

In order to perform its intended functions, an implantable electronic medical device must have an energy source, e.g., a battery. Because the device is implanted in a patient and often performs life sustaining functions, the battery must be extremely reliable and should last as long as possible in order to delay the surgery required to explant or replace the device. Additionally, to prevent harm to the patient from failure of the medical device due to failure of the battery, most such electronic medical devices are configured to provide a signal to the patient or physician indicating that the end of life (EOL) of the battery is approaching. This signal is also referred to as the recommended replacement time (RRT) notification (or signal) for the device.

A well-known characteristic of implantable electronic medical devices, in particular implantable cardioverter-defibrillators (ICDs) and pacemakers, is that the mix of chemicals of the battery used within the device changes as the battery gets older and more depleted, thereby causing the output voltage of the battery to decrease. This characteristic is in fact used to help predict when it is time to replace the device with one having a new battery. Thus, it is common to have the ICD or pacemaker regularly monitor the terminal battery voltage, or output voltage. If the output voltage of the battery drops below a preset threshold, the recommended replacement time (RRT) signal, or equivalent flag or trigger, is initiated.

A number of different types of batteries are known and used in implantable electronic devices, for example lithium iodine batteries, lithium silver chromate and silver vanadium oxide (SVO) batteries. These different battery types have different characteristics that may be useful for different purposes. Increasingly, SVO batteries are being chosen by manufacturers for use in certain implantable electronic devices, particularly implantable cardioverter-defibrillators.

Most ICDS, pacemakers and other implantable electronic medical devices manufactured today include one or more microprocessors. These microprocessors operate most efficiently and reliably under conditions of steady, predictable voltage from the energy source. Because silver vanadium oxide (SVO) batteries maintain a relatively flat voltage during most of their later life, they are particularly well suited to use in these devices. Unfortunately, this advantageous feature of SVO batteries is also disadvantageous. The disadvantage is that it is difficult to predict, using voltage alone, when the battery will fail and thus at what voltage threshold the recommended replacement time (RRT) signal should be activated.

SVO batteries, as well as other batteries, have an additional disadvantage, particularly when used in ICDs. The primary function of an implantable cardioverter-defibrillator (ICD) is to sense the occurrence of an arrhythmia, and to automatically apply an appropriate shock therapy to the heart aimed at terminating the arrhythmia. For example, if the ICD senses that the patient's heart is fibrillating, i.e., beating in a rapid, uncoordinated manner, then the ICD automatically delivers a high current shock to the patient's heart to defibrillate the organ. ICDs typically operate by first detecting the arrhythmia, then rapidly charging one or more storage capacitors contained within the device, and then quickly discharging the capacitor(s) to deliver the life saving shock therapy. Rapidly charging a capacitor, however, creates a severe load on the battery. If the battery's internal impedance is high, the battery is unable to provide adequate voltage to quickly, fully charge the capacitor. This can result in a delay in the delivery of the defibrillating shock or even in complete failure of the ICD.

The internal impedance of a battery is dependent not only upon the age of the battery, but also upon its usage history. For example, if the battery is discharged rapidly and/or frequently, its internal impedance rises very little. If, on the other hand, the battery is discharged very slowly and is not used to deliver a shock for a number of months, the internal impedance may increase very significantly. Thus, relying on the age of the implanted device or measuring only its terminal battery voltage in order to determine the recommended replacement time for the device provides an inaccurate indication of the remaining longevity of the battery. This is particularly true where the device is an ICD which may be called upon to perform its intended function(s) only infrequently.

Measuring terminal battery voltage not only inadequately accounts for the battery's internal impedance, it also can result in a significant waste of battery life where the battery has a flat voltage during the latter stages of its life, such as do SVO batteries, and where a battery voltage replacement threshold is selected that is near or the same as such flat voltage. In order to avoid the risk of failure of the SVO battery, ICD manufacturers carefully and conservatively select the RRT signaling voltage threshold. Generally, manufacturers set this voltage threshold between about 2.485 and 2.55 volts per cell. While these thresholds help ensure that the device will be replaced prior to battery failure, they can also result in a significant loss of valuable ICD usage, because a substantial amount of energy may yet remain in the battery when the output voltage is at these conservative thresholds.

What is needed is a simple, efficient, safe means of determining the recommended replacement time for an implantable electronic medical device, particularly an ICD, that is protective of patient safety yet maximizes battery energy usage.

SUMMARY OF INVENTION

The subject matter disclosed and claimed herein advantageously addresses this and other needs by providing an improved method for determining the recommended replacement time for implantable electronic medical devices, particularly implantable cardioverter-defibrillators. Further, provided herein are improved implantable electronic medical devices employing the improved method.

The methods and devices described herein do not require significant additional hardware, such as additional resistors or current generators, to operate. Therefore, the monitoring and signaling of the recommended replacement time requires very little additional energy from the battery and no significant additional weight or volume is added to the implantable device.

In one embodiment, the improved method entails independent measurement of at least two different indicators of battery strength, at least one of which is affected by the battery's internal impedance. As used herein "battery strength" connotes the ability of the battery to continue to provide an electrical charge, i.e., electrical current, at a sufficient operating potential, i.e., voltage, within a sufficiently rapid time period for the implantable medical device to perform its intended function. Thus, battery strength effectively provides a measure of remaining battery life. In this method, if any of the battery strength indicators falls beyond the predetermined threshold for that indicator, then an RRT signal is issued.

Thus, in a preferred method described herein, terminal battery voltage is used as one indicator of battery strength that is measured independently of any other indicators of battery strength. The terminal voltage is periodically measured and an RRT signal is issued if the voltage falls below a predetermined threshold voltage. A second indicator of battery strength used in this preferred method is capacitor charge time. As with the measuring of terminal voltages the capacitor charge time is periodically monitored, independent of the periodic measurement of the battery terminal voltage. The capacitor charge time is preferably measured during capacitor reformation, and if it exceeds a predetermined maximum threshold time and is confirmed, as described below, then an RRT signal is issued.

Additionally, the capacitor charge time may be measured during therapeutic shock delivery, and if that time is confirmed to exceed the predetermined threshold, then an RRT signal is issued. Because, the capacitor charge time is dependent, in part, upon the internal impedance of the battery, its measurement provides additional protection to the patient from device failure due to battery failure and permits a more accurate indication that the battery's end of life is approaching.

Also contemplated by the present invention, is an implantable cardioverter-defibrillator (ICD) employing the above-described method. Such an ICD includes a battery; control logic and timing circuitry; a capacitor, chargeable by the battery; voltage measuring means, capable of periodic measurement of battery terminal voltage; capacitor reforming means, capable of periodic capacitor reformation; charge-dumping means for dumping the charge of the capacitor; capacitor charge timing means; and RRT signaling means.

In operation, the voltage measuring means periodically determines the battery's terminal voltage. If the voltage is equal to or below a predetermined minimum threshold level then the RRT signaling means is activated. If the voltage is above the threshold, then the control logic and timing circuitry determines whether it is time to perform the periodic capacitor reformation. If so, the capacitor is reformed by the capacitor reforming means. If, during capacitor reformation (or at other programmed times, such as during delivery of therapeutic shock), the capacitor charge time, as measured by the charge timing means, exceeds a predetermined maximum threshold time, then the capacitor's charge is dumped by the charge-dumping means and the capacitor is recharged. If the charge timing means again measures a charge time greater than the maximum threshold time, the RRT signaling means is activated and a signal issued. If the charge time is less than the threshold, then the device returns to its periodic monitoring of battery voltage and periodic capacitor reformation. Additionally, in this preferred embodiment, the capacitor charge time associated with the therapeutic discharge of the ICD is measured, in the same manner just described. This provides an extra measure of safety for the device.

In an alternative embodiment of the improved method described herein, at least two indicators of battery strength are used together to determine when to issue an RRT signal. As with the previously described method, this alternative method includes the periodic monitoring of a first and at least one second indicator of battery strength and issuing an RRT signal if any indicator falls beyond its predetermined threshold. In addition to this independent monitoring of at least two indicators of battery strength, however, this alternative embodiment also involves determining whether a first indicator has been close to its predetermined threshold long enough to suggest the battery's end of life may be near and then measuring at least one second indicator of battery strength to determine if an RRT signal should be issued.

One preferred embodiment of this alternative method of determining the recommended replacement time, which is discussed in detail below, involves the use of terminal battery voltage as a first indicator of battery strength and capacitor reforming charge time as a second indicator. In this embodiment, each indicator is periodically monitored. As with the previously described embodiment, if the terminal battery voltage falls below, or the capacitor reforming charge time exceeds, the predetermined voltage or time, respectively, then an RRT signal is issued. If on the other hand, the terminal battery voltage is in a predetermined range above, but close to the predetermined threshold, then that fact is registered on a battery voltage status register. Once a predetermined number of low voltage incidents have been registered, the capacitor reforming charge time is measured. If that value exceeds the predetermined maximum charge time and is verified, then an RRT signal is issued. If the charge time is less than the predetermined value, the battery voltage status register is reset to an appropriate value, e.g., zero, and the device resumes normal monitoring and operating functions.

Also contemplated herein is an implantable cardioverter-defibrillator (ICD) employing the alternative method wherein at least two indicators of battery strength are used together to determine when to issue an RRT signal. In a preferred embodiment, the ICD includes a battery, control logic and timing circuitry including therein defibrillation circuitry for carrying out the defibrillation function of the ICD and battery voltage status register for registering occurrences of low battery terminal voltage; a capacitor, chargeable by the battery; voltage measuring means for regularly measuring the battery's terminal voltage; capacitor reforming means; charge-dumping means for dumping the charge of the capacitor; charge timing means for measuring the time for charging of said capacitor; and RRT signaling means.

In operation of this preferred embodiment, the battery's voltage is periodically monitored. If the voltage falls below a predetermined threshold, then an RRT signal is issued. If the voltage falls within a predetermined range close to the threshold value, then it is determined whether the battery status register is at its predetermined maximum level. If it is not, the status register is incrementally increased. If the battery status register is at its maximum, then the capacitor is immediately reformed and the charge time determined. If the charge time is confirmed to exceed its predetermined maximum, then an RRT signal is issued. If the charge time is less than the predetermined threshold then the battery status register is reset to zero and the ICD resumes its normal operating and monitoring functions.

Additionally, the capacitor is periodically reformed and its charge time may thus be measured independently of the periodic measurement of battery voltage. If, during this periodic reformation, the capacitor charge time is confirmed to exceed the predetermined threshold charge time, an RRT signal is issued. If the charge time does not equal or exceed the maximum threshold, then the battery status register is reset to zero and the ICD returns to its normal functions.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
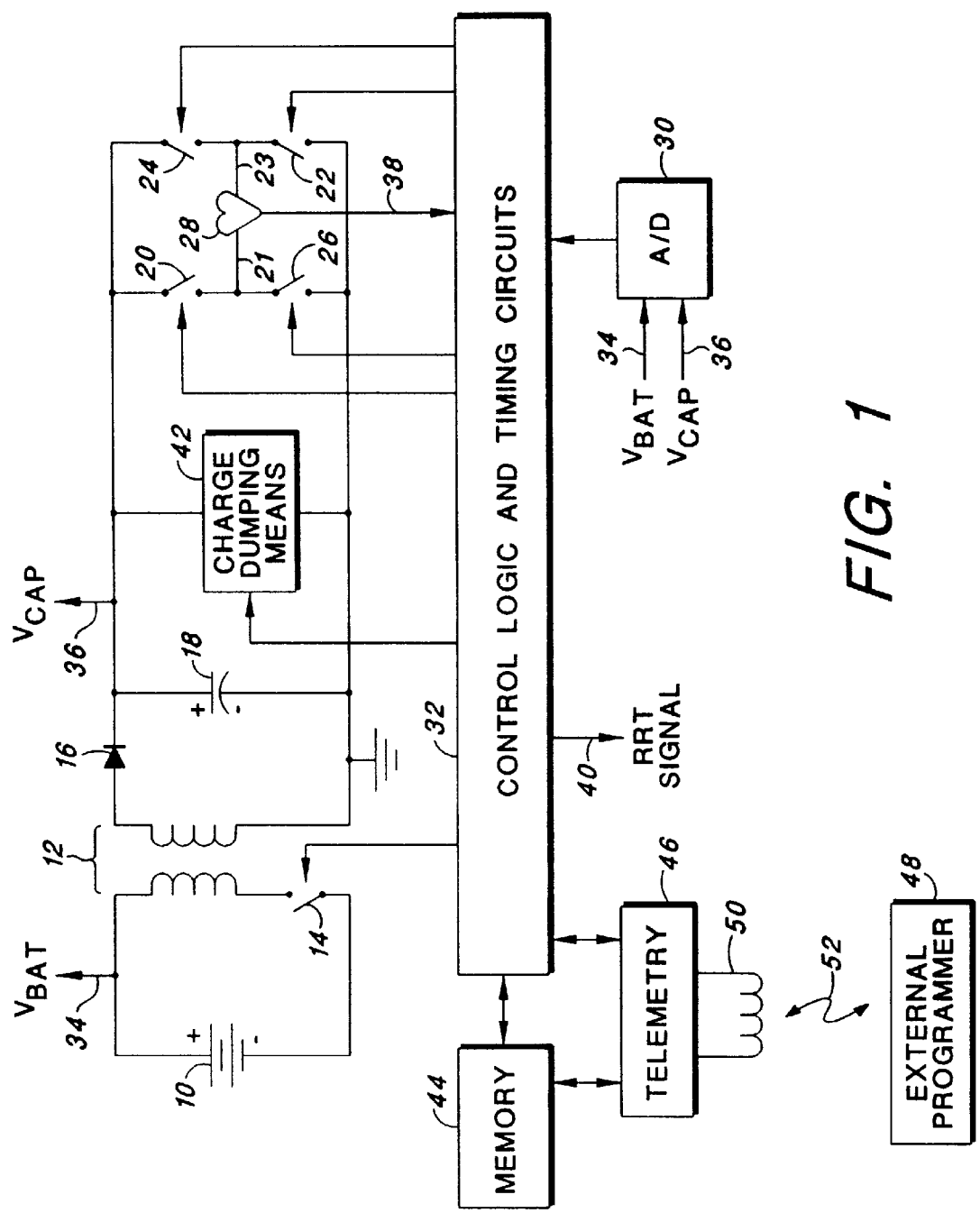
FIG. 1 is a is a general schematic diagram of a preferred embodiment of an implantable cardioverter-defibrillator (ICD) employing the improved method for determining the recommended replacement time (RRT) for such a device.

Turning first to FIG. 1, there is shown a general schematic diagram of an implantable cardioverter-defibrillator (ICD) of a type with which the present improved methods may be used. A brief explanation of the ICD will first be presented in order to lay the foundation for the description of the invention—which relates to just one feature included within the ICD—that will follow.

Referring then to FIG. 1, a battery 10 drives a current through a primary winding of transformer 12 on an interrupted basis controlled by switch 14. The voltage induced at a secondary winding of the transformer 12 is steered through a diode 16, and stored as a moderate to high energy charge on the capacitor 18. Control logic and timing circuits 32 (hereafter, "control/timing" circuit 32), contained within the ICD, typically includes digital timers, registers and counters as well as a microprocessor programmed to carry out control and timing functions, such as sensing heart activity through an appropriate sensor or electrode and lead 38. At the time a defibrillating or cardoverting shock is needed, the timing/control circuit signals switches 20 and 22 to close, thereby allowing the delivery of a high current through leads 21 and 23 and the heart 28 in one direction. After a short period of time, for example 4–6 ms, the control/timing circuit 32 re-opens switches 20 and 22 and signals switches 24 and 26 to close. This allows delivery of another high current through leads 21 and 23 and the heart 28 in the opposite direction of the first current. Such biphasic shocks, or biphasic current pulses, have been shown to defibrillate very effectively and thus are common practice in the art.

Also shown in FIG. 1 are components used in carrying out the present invention. In particular, an A/D converter 30 senses both the battery terminal voltage ($V_{BATT}$) 34 and the capacitor voltage ($V_{CAP}$) 36 and converts these analog readings into digital signals which are then communicated to the control/timing circuit 32. The control/timing circuit 32 monitors these communications on a periodic basis, which period may be programmed into the control/timing circuit 32. In this way, the capacitor charge time is determined. The control/timing circuit retrieves, from the memory 44, the predetermined minimum battery voltage (X) and/or maximum capacitor recharging time (Y) and compares these values to the sensed values. The predetermined $V_{BATT}$ and/or $V_{CAP}$ may be programmed into the memory 44 by way of telemetry circuit 46 coupled to external programmer 48 as is known in the art. If appropriate, an RRT signal 40, is issued as discussed in detail below; otherwise, the control/timing circuit continues with its periodic monitoring.

As is well known to those of skill in the art, capacitor recharge time 36 is determined by reference to the measurement of the capacitor's output voltage time as the capacitor is recharged following a discharge. The discharge may be the result of a therapeutic shock or may be the result of a routine capacitor reformation process involving the charge-dumping means 42, as illustrated in FIG. 1. With respect to determining whether to issue an RRT signal, the control/timing circuit may be, and preferably is, programmed to disregard the capacitor charge time measured during a therapeutic discharge.

As stated above, the control/timing circuit 32 is coupled to a memory circuit 44. Prior to and/or contemporaneously with implantation of the ICD, the memory circuit 44 is programmed with the operating parameters to be used by the control/timing circuit 32. Such operating parameters include, but are not limited to, the minimum permissible battery terminal voltage; the maximum permissible capacitor charge time and the frequency with which battery terminal voltages and capacitor charge time are to be evaluated. Advantageously, such operating parameters may be noninvasively programmed into the memory 44 through a telemetry circuit 46, in telecommunicative contact with an external programmer 48 by way of a suitable coupling coil 50. The coupling coil 50 may serve as an antenna for establishing a radio frequency (rf) communication link 52 with the external programmer 48; or the coil 50 may serve as a means for inductively coupling data to and from the telemetry circuit 46 from and to the external programmer 48. Further, such telemetry circuit 46 advantageously allows status information relating to the operation of the ICD, as contained in the control/timing circuit 32 or memory 44, to be sent to the external programmer 48 through the established link 52.

The design, operation and use of the telemetry circuit 46 and external programmer 48 to selectively program operating parameters into the memory 44, or to selectively monitor the operating status of the ICD, may be the same as are known in the art. See, e.g., U.S. Pat. Nos. 4,809,697 (Causey, III et al.) and 4,944,299 (Silvian), incorporated herein by reference.

Typically, the microprocessor, or other similar processing circuit upon which the control/timing circuit 32 is based, includes the ability to process or monitor input signals (data) in a prescribed manner, for example, as controlled by program code stored in the memory 44. The use, design, and operation of microprocessor-based control circuits to perform timing and data analysis functions is also known in the art. Alternatively, the control/timing circuit 32 may be realized using conventional logic circuits, for example, registers, flip-flops, logic gates, and the like, as is likewise known in the art. The details of the design and operation of the control/timing circuit 22 are not critical to the present invention. Rather, any suitable control/timing circuit 22 may be used that carries out the functions described herein.

Figure 2:
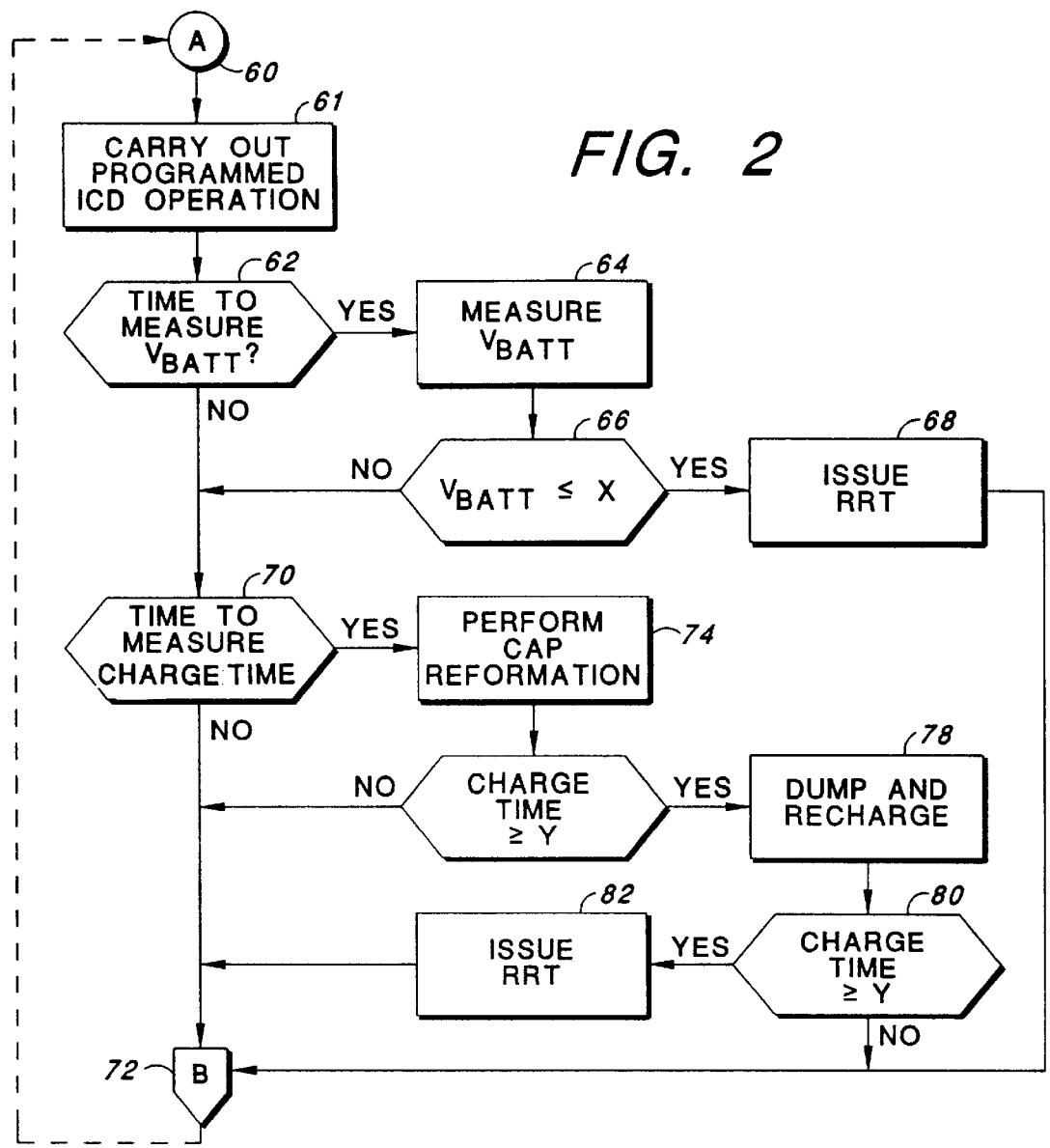
FIG. 2 is a flow diagram illustrating the steps performed by an implantable medical device in determining whether to issue an RRT signal in accordance with one embodiment of the invention.

As stated, FIG. 2 is a general diagram of an ICD. Those of skill in the art will readily appreciate that the ICD may have other capabilities not enumerated herein and not necessary for the operation of the present invention. For example, the device may include pacing circuitry (such as is commonly provided in an implantable single or dual chamber pacemaker) and/or may have additional sensing capabilities and/or may be designed to provide a tiered therapy. Any implantable medical device, particularly any implantable cardioverter-defibrillator, having a battery; capacitor, chargeable by the battery; means for dumping and recharging the capacitor; and monitoring/signaling means may be used and is contemplated for use with the invention described herein.

As stated above, various battery types are well known in this art and variously used within implantable medical devices. The batteries used in implantable medical devices include one or more cells joined in series. For purposes of discussing the specific voltage values herein, it will be assumed that the battery is a single cell battery. This is done merely to simplify the specific examples provided herein. Those of ordinary skill in the art will readily appreciate that the total voltage of a battery is equal to the voltage of a single cell multiplied by the total number of cells when the cells are connected in series(which is usually the case). Further, those of ordinary skill in the art know that the electrochemistry of the battery determines the cell voltage. For example, a silver vanadium oxide (SVO) battery produces about 3.0 volts per cell and an SVO battery containing two cells produces about 6 volts total. Thus, if a minimum battery terminal voltage threshold for an SVO battery is set at 2.35 volts, it is equivalent to a setting of about 4.7 volts for a two cell, six volt SVO battery.

The use of electrolytic capacitors within an ICD device for the storage of energy necessary for producing high voltage shocks during cardioversion\defibrillation therapy is currently universal. However, use of these electrolytic capacitors for a device with an estimated lifetime of several years necessitates periodic reformation to maintain the physical characteristics of the capacitors. There are a number of ways in which a capacitor, used in an implantable medical device, may be reformed. The general process for capacitor reformation, however, is based on the chemical composition of electrolytic capacitors and the chemical reactions thereof, which are well known in the art.

For the purposes of practicing specific embodiments of the methods and devices described herein, it is important that the reformation process include the complete discharge of the fully charged capacitor and its subsequent full recharge. Some methods of capacitor reformation known to those of skill in the art involve fully charging the capacitor then permitting the charge to leak for a specified length of time. Employing such a "leaking" method of reformation, however, does not require complete discharge of the capacitor prior to recharging.

Thus, to the degree any embodiment of the method disclosed and claimed herein relies upon measurement of capacitor charging time, and its comparison of the capacitor charging time to a threshold value to determine the recommended replacement time for the device, that embodiment must include the complete discharge of the fully charged capacitor prior to or contemporaneously with measurement/determination of the charging time, or use a corrected charge time based on the residual capacitor voltage found before the initiation of a new charge cycle. It will be appreciated that embodiments of the methods and devices described herein that include measurement of capacitor charge time as an indicator of recommended replacement time may additionally include almost any other method of capacitor reformation.

Turning now to a preferred embodiment of the present method, FIG. 2 is a flow diagram illustrating the operation of an ICD in determining whether to issue an RRT signal. The illustrated method involves independent measurement of at least two different indicators of battery strength, at least one of which is affected by the battery's internal impedance. Such a method inexpensively provides a more effective indication of recommended replacement time while maintaining patient safety.

Each main step of the operation shown in FIG. 2 is represented as a block or box, having a corresponding reference numeral. Rectangular-shaped boxes or blocks typically represent a process or event or series of events that occur in order to realize the function indicated, whereas diamond-shaped (or hexagonal-shaped) boxes or blocks usually represent a determination or decision that must be made, which decision typically has at least two possible outcomes, e.g., YES or NO.

It is noted that the steps shown in FIG. 2 to control an ICD device, as well as those shown in the flow chart of FIG. 3 described below, may be carried out by those of skill in the art using the control logic and timing circuit 32 based on either a programmed microprocessor, a hardwired state machine logic circuit, or other equivalent circuits. Indeed, the present invention is not dependent upon or limited by a specific type of circuitry or electronic programmable device used to control the ICD. Rather, it is contemplated that the invention may be carried out using a wide variety of components, circuits, and/or programmable devices.

It is noted that in the operation of a typical ICD device, several different functions and operations may be carried out, many of which are not relevant to the present invention. All such operations may be included in the main flow branch or loop shown on the left side of FIG. 2 that begins with the "A" start block 60, continues at block 61, and further includes the checks indicated at blocks 62 and 70, continuing on to the "B" connector block 72. Such main flow branch is hereafter referred to as the "main control loop A-B" or "A-B control loop".

Referring now to FIG. 2, in this first preferred embodiment of the invention, at least two determinations are made at some point in the main control loop A-B. A first determination made is whether or not it is time to measure the battery terminal voltage ($V_{BATT}$) 62. Typically, this measurement is taken on a scheduled basis, for example, every 12, 24 or 48 hours, with a period of 24 hours generally being preferred. This scheduled period is normally preprogrammed into the ICD either prior to or contemporaneously with implantation of the device. If it is not time to measure the battery terminal voltage (NO branch of block 62), then control continues through the A-B control loop. If it is time, the battery terminal voltage is measured (block 64). If the voltage is less than or equal to a predetermined minimum threshold voltage X ($V_{BATT}$pX) (block 66), then an RRT signal is issued (block 68). If, however, the battery terminal voltage is greater than the predetermined threshold, flow proceeds back to the A-B control loop, for the second determination; that is whether it is time for the periodic reformation of the capacitor (block 70). Typically, capacitor reformation will be performed on a scheduled basis, for example, about once every 30 to 70 days, with once every 55 to 65 days being preferred and once every 64 days, or about bi-monthly, being further preferred.

If it is not time to perform the capacitor reformation (NO branch of block 70), then control continues through the A-B control loop. If it is time (YES branch of block 70), then capacitor reformation is preformed (block 74) by dumping the capacitor's stored charge and recharging it. Once discharged, the capacitor is recharged and the capacitor charge time is determined (block 76); for example, by reference to the measurement of the capacitor's output voltage over time during recharge. If the recharge time is not greater than or equal to a predetermined maximum threshold, Y, then the flow returns to the A-B control loop. If, on the other hand, the recharge time exceeds or is equal to the maximum recharge time ($V_{CAP}$pY) (YES branch of block 76), the capacitor charge is again dumped and the capacitor is reformed (block 78) and the capacitor charge time is again determined (block 80). Should the charge time still exceed or equal the maximum charge time (YES branch of block 80), an RRT signal is issued (block 82). If this second recharge time is less than the maximum threshold (NO branch of block 80), the flow returns to the A-B control loop. This is because the extended charge time might have been due to a deformed capacitor and not a weak battery.

As an added safety factor, the preferred embodiment may also be programmed to determine the capacitor charge time during delivery of a therapeutic shock. As discussed above, the primary function of an ICD is to provide therapeutic shocks to the heart as needed. To do this, the ICD charges the capacitor to a specified level and then, effectively, dumps the charge into the heart of the patient. If the capacitor charge time associated with charging the capacitor(s) to the specified level equals or exceeds the predetermined maximum charge time, then the charge time is again measured to confirm that it does indeed exceed or equal the maximum charge time. That is, for a second time, the charge on the capacitor is dumped, the capacitor recharged and the recharge time measured. If it is confirmed that the capacitor charge time equals or exceeds the maximum threshold, then an RRT signal is issued.

Thus, in this first preferred embodiment, two different parameters, both predictive of battery end of life (EOL), are independently, periodically measured to determine when to issue the RRT signal. Such method advantageously provides more efficient use of the battery life, not only because it permits a more accurate measurement of EOL, but also because it requires very little additional energy from the battery to execute.

An implantable cardioverter-defibrillator (ICD) employing the above described method is also contemplated as part of the invention described and claimed herein. Such an ICD includes a battery; control logic and timing circuitry; a capacitor, chargeable by the battery; voltage measuring means, capable of periodic measurement of battery terminal voltage; capacitor reforming means, capable of periodic capacitor reformation; charge-dumping means for dumping the charge of the capacitor; charge timing means, and RRT signaling means. In operation, the voltage measuring means periodically determines the battery's terminal voltage. The control logic and timing circuitry (control/timing circuitry) compares the measured battery terminal voltage with a minimum threshold voltage, previously stored in the control/timing circuitry. If the measured voltage is equal to or below that minimum threshold, the control/timing circuitry activates the RRT signaling means and a signal is issued.

Various types of RRT signaling means are known to those of skill in the art and any such means, compatible with the method described herein, may be used. For example, the signal may be stimulation of a muscle located near the implanted device, or it may be an audible signal, or it may be a fluctuation in the pacing of the patient's heart (where the implanted device is capable of pacing). See U.S. Pat. No. 4,295,474 (Robert E. Fischell), for example of such RRT signals, that would be amenable to use herein.

If the battery terminal voltage, as measured by the voltage measuring means, is above the minimum threshold, then the control/timing circuitry determines whether it is time to perform the periodic capacitor reformation. As stated previously, this time period is preprogrammed into the ICD before or contemporaneously with implantation. When appropriate then, the capacitor is reformed by the capacitor reforming means. Capacitor reforming means are well known to those of ordinary skill in the art. As stated above, all that is required of the capacitor reforming means employed herein is that it involve the complete discharge of the fully charged capacitor and its subsequent full recharge, or at least sufficient recharge to enable a charge time constant to be determined. (Once a charge time constant has been determined, the recharge time can be estimated using that constant.)

During capacitor reformation, the charge timing means measures the charge time. The control/timing circuitry compares the measured capacitor charge time with the predetermined maximum threshold time. If the measured charge time is less than the maximum threshold, then the ICD returns to its normal functions until it is again time to measure the terminal battery voltage or time to reform the capacitor. If the measured charge time exceeds the maximum threshold, an issue arises as to whether the excessive charge time is an indication that the battery internal impedance is high or an indication that the capacitor is leaky (deformed) and needs a reformation. As is known to those of skill in the art, a second reformation of the capacitor will restore it to about 99% efficiency, if it is leaky. Thus, the charge dumping means is activated to dump the charge from the capacitor and fully recharge it. Again, the charge time is measured by the charge timing means. If the capacitor charge time is now less than the maximum threshold, the ICD returns to its normal functions. If, on the other hand the capacitor charge time again exceeds the maximum threshold, the control/timing circuitry activates the RRT signaling means and an RRT signal is issued.

In the above-described embodiment, the capacitor charge time associated with the therapeutic usage of the ICD is also measured. This provides an extra measure of safety, as it is an otherwise unscheduled monitoring of the capacitor charge time. That is, monitoring the capacitor charge time of a therapeutic shock is in addition to, not a replacement of, the preprogrammed periodic monitoring of this parameter. As with the periodic measurement of capacitor charge time, measurement during a therapeutic shock is confirmed to be above the maximum threshold before an RRT signal is issued. Thus, the procedure is the same as just described with respect to the periodic measurement of capacitor charge time: the charge time of the therapeutic shock is measured, and, if that time is in excess of the maximum threshold, the capacitor charge is dumped, the capacitor recharged and the charge time remeasured. If the charge time is again in excess of the maximum threshold, then the RRT signaling means is activated and an RRT signal issued.

Figure 3:
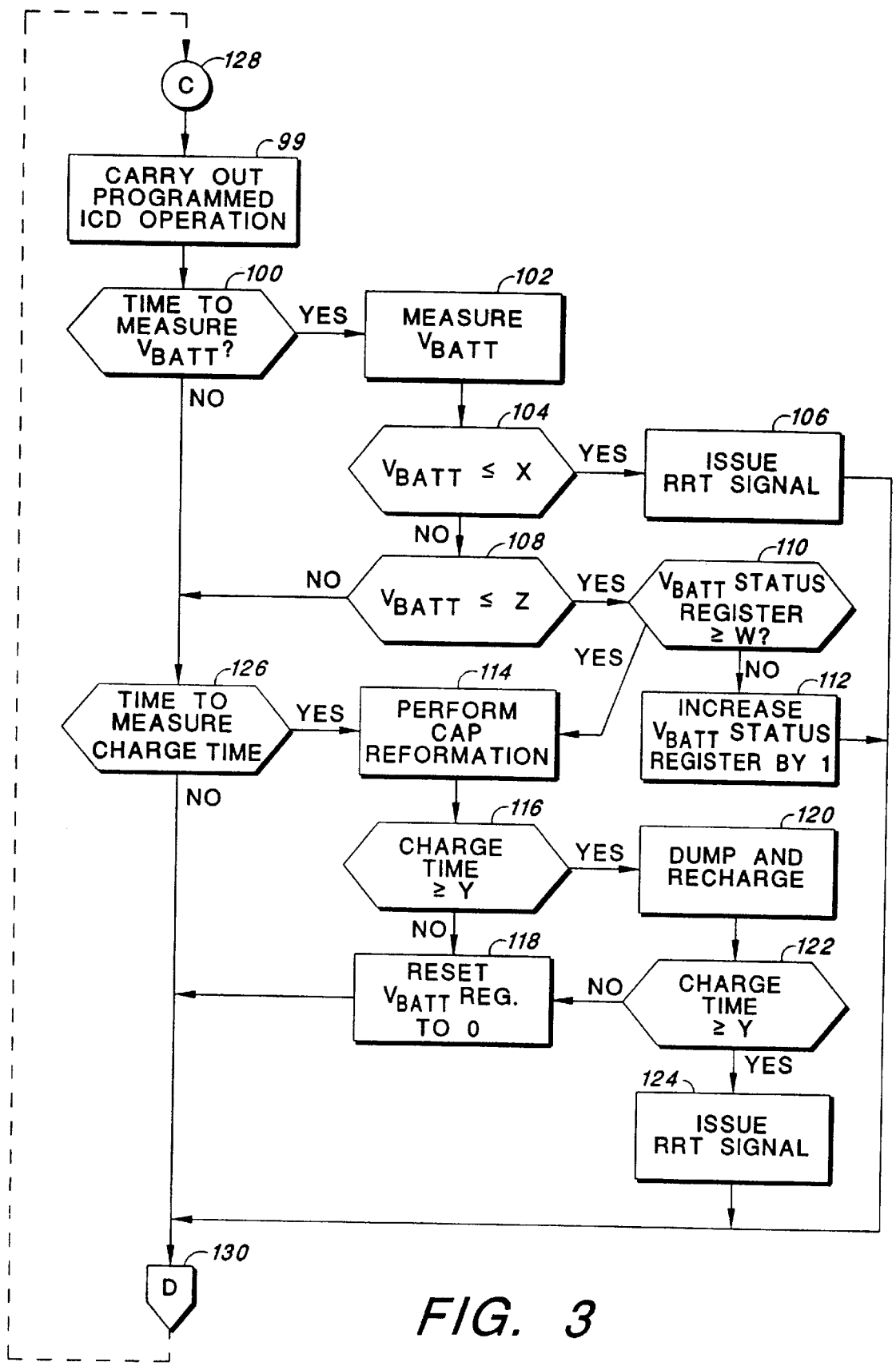
FIG. 3 is a flow diagram illustrating the steps performed by the ICD of FIG. 1 in determining whether to issue an RRT signal in accordance with an alternative embodiment of the invention.

Turning now to FIG. 3, a flow diagram is shown of an alternative embodiment of the present invention. As discussed above, this alternative embodiment involves not only the independent monitoring of at least two indicators of battery strength, but also provides for the dependent monitoring of these same indicators, for the purpose of determining when to issue an RRT signal. As with FIG. 2, the alternative method of FIG. 3 is illustrated as a branch of a main flow (or control) loop of an ICD control logic and timing circuit, shown on the left side of FIG. 3. Several operations and functions may be performed by the ICD and included in this main branch or loop which begins with the "C" start box 128, continues at block 99, and further includes the checks indicated at blocks 100 and 126, continuing on to the "D" connector block 130. This main control loop is hereinafter referred to as the "main control loop C-D" or the "C-D control loop".

Referring then to FIG. 3, a first determination made, while in the C-D control loop, is whether it is time to measure the battery terminal voltage ($V_{BATT}$) (block 100). As with the previously described embodiment, the frequency with which battery terminal voltage is to be taken is programmed into the ICD either prior to or contemporaneously with implantation of the device. For example, such frequency may be 24 hours; however, it will be appreciated that this measurement may be taken more or less frequently. If it is not time to measure the battery terminal voltage (NO branch of block 100) then flow proceeds to the second determination of the main control loop C-D, namely, whether it is time for the periodic reformation of the capacitor (block 126). Assuming it is not time for capacitor reformation (No branch of block 126), flow continues through the C-D control loop, as indicated.

If it is time to measure the battery terminal voltage (YES branch of block 100), then the terminal voltage is so measured 102. If the battery terminal voltage is less than or equal to the predetermined threshold X ($V_{BATT}$pX) (YES branch of block 104), an RRT signal is issued (blocked 106). If, on the other hand, the voltage is higher than the threshold (No branch of block 104), flow proceeds to block 108, where a determination is made as to whether the battery terminal voltage is less than or equal to an intermediate threshold Z ($V_{BATT}$pZ), where Z is greater than X. If $V_{BATT}$ is not less than or equal to the intermediate threshold (NO branch of block 108), then flow proceeds back to the main control loop C-D and on to block 126, which is discussed further below.

If $V_{BATT}$ is less than or equal to the intermediate threshold value (YES branch of block 108), then flow proceeds to block 110, and a determination is make as to whether a battery status register is at its maximum count W (i.e., is the countpW). If it is not (NO block of branch 110), then the status register is incrementally increased (block 112), and flow proceeds back to the main control loop C-D. As noted above, the control logic and timing circuit 32 (FIG. 1) includes registers for storing digital data used in the control of the ICD function. One such register, for the purposes of this embodiment, is a battery status register. The increment for counting the occurrences of low battery terminal voltage is not critical and is set at one for the purposes herein. In this preferred embodiment, the maximum permissible count on the battery status register, "W", is set for 15, as will be discussed further below.

Returning to block 110, if the battery status register is at its maximum count (YES branch of block 110), that is fifteen, then capacitor reformation is immediately performed (block 114) by completely discharging the capacitor and recharging it. The capacitor charge time is determined (block 116) during the reformation, as previously described. If the charge time is not greater than or equal to the predetermined maximum threshold (pY) (NO branch of block 116), then the battery status register is reset to zero (block 118) and flow proceeds back to and through the C-D control loop. If the capacitor charge time is greater than or equal to the maximum threshold (YES branch of block 116) then the capacitor is again discharged of its entire charge and recharged (block 120) and the charge time determined (block 122). If the charge time is still equal to or exceeds the maximum threshold (YES branch of block 122), then an RRT signal is issued (block 124). If, however, the charge time is less than the maximum threshold (NO branch of block 122), the battery status register is reset to zero (block 118) and flow proceeds back to and through the main control loop C-D.

In addition to reformation of the capacitor depending upon the measured battery terminal voltage, the capacitor is periodically reformed (block 126) in the course of the main control loop C-D. As described above, this periodic reformation will normally be programmed to occur once a month, once every two months or once every two-and-a-half months or other selected interval, with a setting of every other month being generally preferred for many patients. Assuming then that it is time for such a regularly scheduled reformation (YES branch of block 126), flow proceeds from block 126 to block 114 and through the reformation process as just described.

Thus, it will be appreciated by those of skill in the art that an ICD employing the alternative embodiment illustrated in FIG. 3 provides the possibility of earlier detection of the battery's approaching end of life, and therefore may provide an extra safety feature. This is because the capacitor charge time is measured more frequently when the battery voltage repeatedly dips to or below the intermediate threshold. This alternative embodiment is particularly useful when the minimum battery voltage threshold (X) is set very near the end of life of the device. It permits the higher intermediate threshold value to be used, in conjunction with capacitor charge time, to provide an early warning of the approaching EOL, while protecting against a dramatic drop in battery terminal voltage by the daily monitoring at the critical minimum threshold and automatic RRT signal issuance when that threshold is met.

Further contemplated herein as part of the invention, is an implantable cardioverter-defibrillator (ICD) employing the above-described alternative method FIG. 3) wherein at least two indicators of battery strength are used together to determine when to issue an RRT signal. In a preferred embodiment, the ICD includes a battery, control logic and timing circuitry including therein defibrillation circuitry for carrying out the defibrillation function of the ICD and battery voltage status register for registering occurrences of battery terminal voltage below an intermediate threshold; a capacitor, chargeable by the battery; voltage measuring means for regularly measuring the battery's terminal voltage; capacitor reforming means; charge-dumping means for dumping the charge of the capacitor; charge timing means for measuring the time for charging the capacitor; and RRT signaling means.

In operation of this alternative embodiment, the battery's voltage measuring means periodically measures the battery terminal voltage as directed by the control logic and timing circuitry (control/timing circuitry). The control/timing circuitry compares the measured voltage to the predetermined minimum threshold. If the voltage measures less than the minimum thresholds then the RRT signaling means is activated and an RRT signal is issued. If the voltage measures greater than the minimum threshold but less than or equal to a predetermined intermediate threshold, which intermediate threshold together with the minimum threshold defines a range that is close to the minimum threshold value, then the control/timing circuitry determines whether a count contained in a battery status register, located within the control/timing circuitry, is at its predetermined maximum level.

Upon determination by the control/timing circuitry that the status register has not reached its maximum count, that count is incrementally increased. If, on the other hand, the battery register status has reached its maximum count, then the control/timing circuitry activates the capacitor reforming means and capacitor reformation is performed. During capacitor reformation, the charge timing means measures the time for capacitor charging. The control/timing circuitry compares the measured capacitor charge time with the predetermined maximum threshold. If the charge time is less than the maximum threshold, then the device returns to its normal functions, including periodic battery terminal voltage measurement and periodic capacitor reformation.

If it is determined that the capacitor charge time is equal to or exceeds the maximum threshold, then the charge-dumping means is again activated and the charge on the capacitor is dumped and the capacitor recharged. Again, the charge timing means measures the capacitor charge time and the control/timing circuitry compares this measured time to the maximum threshold. If the charge time is again equal to or greater than the maximum threshold, then the RRT signaling means is activated and an RRT signal issued. If, however, the charge time is now less than the maximum threshold, then the battery status register count is reset to an appropriate value, e.g., zero, and the ICD resumes its normal functions.

In addition to the just described unscheduled capacitor reformation and charge time measuring, the capacitor is reformed and its charge time measured on a preprogrammed periodic basis. The periodic reformation of the capacitor is performed in the same manner as above; that is, the capacitor reforming means is activated and the capacitor reformed while the charge timing means measures the charge time. As discussed above, if the charge time is confirmed to exceed the maximum threshold, an RRT signal is issued. If the charge time does not equal or exceed the maximum threshold, then the battery status register is reset and the ICD returns to its normal functions.

Obvious variations of the above described embodiments, though not detailed herein, are considered within the scope of the present disclosure. For example, the alternative embodiment illustrated in FIG. 3 may additionally include the ability to measure the capacitor charge time associated with delivery of a therapeutic shock, as is described with respect to the first preferred embodiment (FIG. 2). This variation may optionally include the step of resetting the battery status register upon determination that the capacitor charge time is below its maximum threshold and before re-entering the main control loop C-D.

Another variation, specifically contemplated herein, is an ICD device capable of using different RRT signals to indicate either the source of the signal or its urgency or both. For example, one type of RRT signal may be used to indicate that low terminal battery voltage is the triggering event and a different RRT signal may be used to indicate that excessive capacitor charge time is the trigger for the signal. Alternatively or additionally, a distinguishable RRT signal may be used to indicate that a battery terminal voltage at or below the minimum threshold is the triggering event and therefore, urgent attention to the device is required, with a different signal type indicating that the triggering event is the combination reading of intermediate voltage level and excessive capacitor charge time. Examples of different signals include, but are not limited to, distinctive formats of stimulation current applied subcutaneously to cause a mild tickling sensation and/or distinctive audible warnings and/or temperature changes and/or mechanical motions, etc. Such distinguishable signals are known in the art and thus are not further detailed herein. See for example, U.S. Pat. No. 4,295,474, incorporated herein by reference The embodiments described herein and illustrated in FIGS. 2 and 3 require that certain parameters be programmed into the control logic and timing circuits prior to or contemporaneously with device implantation. These parameters include the minimum and intermediate thresholds of the battery terminal voltage; the frequency with which battery terminal voltage and capacitor charge time are monitored; the maximum threshold of the capacitor charge time; and the maximum count on the battery status register.

Those of skill in the art shall be able to select these parameters based upon the operating characteristics and hardware of the ICD. For example, in selecting the parameters relating to battery terminal voltage and frequency of monitoring, the programmer should consider the type of battery being used and its expected lifetime performance characteristics. Thus, in an ICD where an SVO battery is the preferred battery choice, the flat terminal voltage over the lifetime of the battery is of primary concern. This characteristic of SVO batteries is shown graphically in FIG. 4.

Figure 4:
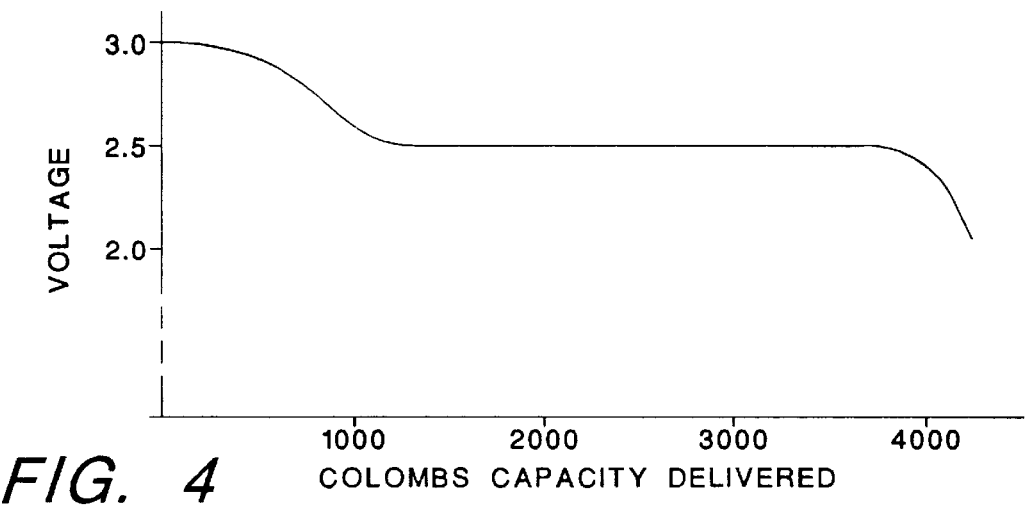
FIG. 4 is a graphic representation of the average voltage output of a silver vanadium oxide (SVO) battery over the course of the battery's life.

As seen in FIG. 4 the output voltage of a typical SVO battery over the course of its life is illustrated. As can be seen, choosing a minimum threshold of 2.5 V would result in a dramatic loss of useful life from the battery; whereas selection of a value of 2.0 V would risk failure of the battery before replacement could be made. Thus, for purposes herein, the minimum battery terminal threshold, for an ICD employing a 3 V per cell, SVO battery, should be set between about 2.0 V and 2.5 V, preferably between 2.2 and 2.4 V, and most preferably at about 2.35 V. Similarly, the intermediate threshold may be selected to be as close as possible to the minimum battery voltage in order to maximize battery usage while minimizing risk of battery failure. According to the battery characteristics illustrated in FIG. 4, the intermediate threshold is preferably set between about 2.3 V and 2.5 V and most preferably is set at about 2.45 V. With respect to the frequency of monitoring of the terminal voltage, as discussed above, this parameter is preferably set between about 12 and 48 hours with daily monitoring (i.e., every 24 hours) being generally preferred.

In addition to minimum and intermediate battery terminal voltage thresholds and a monitoring frequency, maximum capacitor charge time and the frequency of its monitoring are values to be programmed into the ICD either before or at the time of implantation. As is known to those of ordinary still in the art, selecting an appropriate maximum capacitor charge time will depend upon such things as the size and number of the capacitor(s) and the available battery voltage. In the preferred embodiments described herein, it is assumed that the battery is a 3-volt per cell SVO battery and that the capacitor has a total capacitance of between about 50 and 200 $\mu$F, e.g., about 100 $\mu$F, either as a single capacitor or as a total of more than one capacitor. Under these conditions, a maximum capacitor charge time of between about 12 and 17 seconds is appropriate, with a 15 second maximum being preferred.

ICD capacitor reformation, in accordance with the present invention, is performed automatically and the reformation interval is programmable. If no reformation interval is specified, a default interval is used. The default interval may be any suitable value, e.g., 64 days. Those of ordinary skill in the art are familiar with the selection of such a parameter; however, preferred herein is a capacitor reformation frequency of 64 days, i.e., every other month. It will be appreciated that this period may be shorter or longer. Important to consider in selecting the period between reformations is the battery energy required to perform this function, because the capacitor is dumped and fully charged at least once during reformation.

While the invention herein disclosed has been described by means of specific embodiments and applications thereof, numerous modifications and variations could be made thereto by those skilled in the art without departing from the scope of the invention set forth in the claims.

What is claimed is:

1. An implantable cardioverter/defibrillator (ICD) comprising:
    a battery;
    a capacitor, chargeable by the battery;
    voltage measuring means, capable of measuring the terminal voltage of the battery;
    capacitor reforming means, for reforming the capacitor;
    capacitor charge timing means;
    recommended replacement time (RRT) signaling means, for issuing an RRT signal; and
    control logic and timing circuitry having programmable memory, a battery status register and communication means whereby, the control logic and timing circuitry monitors the voltage measuring means and the charge timing means to control the battery status register and the issuance of an RRT signal from the RRT signaling means.

2. The ICD of claim 1, wherein the control logic and timing means is programmed with a minimum battery voltage threshold and an intermediate battery voltage threshold, both for comparison to the measured terminal battery voltage; a maximum capacitor charge time thresholds for comparison to the measured capacitor charge time; and a maximum battery status register counts for comparison to the count contained in the battery status register.

3. The ICD of claim 2, wherein the control logic and timing means controls the battery status register by incrementally increasing the count contained therein when the battery terminal voltage, as measured by the voltage measuring means, is above the minimum battery voltage threshold and below or equal to the intermediate battery voltage threshold.

4. The ICD of claim 3, wherein the control logic and timing means activates the capacitor reforming means when the count on the battery status register equals or exceeds the maximum battery status register count.

5. The ICD of claim 4, wherein the control logic and timing means activates the RRT signaling means to issue a first RRT signal when the battery terminal voltage, as measured by the voltage measuring means, is equal to or below the minimum battery voltage threshold and activates the RRT signaling means to issue a second RRT signal when the capacitor charge time, as measured during capacitor reformation, by the capacitor charge timing means, is equal to or exceeds the maximum capacitor charge time threshold.

6. In an implantable cardioverter/defibrillator (ICD) having a battery, a capacitor, control logic and timing circuitry and a status registers an improved method of determining when to issue a recommended replacement time (RRT), the method comprising the steps of:
    a) periodically measuring a first indicator of battery strength;
    b) comparing the first measurement with a first predetermined threshold;
    c) issuing a first RRT signal in the event the first measurement is equal to or falls beyond the first predetermined threshold;
    d) comparing the first measurement to an intermediate threshold, in the event the first measurement is not equal to or beyond the first predetermined threshold;
    e) determining whether the status register is at a maximum count, in the event the first measurement is equal to or beyond the intermediate threshold;
    f) incrementally increasing the status register in the event the status register is not at the maximum count;
    g) measuring a second indicator of battery strength, which indicator is affected by the internal impedance of the battery, in the event the status register is at the maximum count;
    h) comparing the second measurement to a predetermined second threshold; and
    i) issuing a second RRT signal in the event the second measurement is equal to or beyond the predetermined second threshold.

7. The method of claim 6, further comprising the steps of:
    a) periodically measuring the second indicator of battery strength, wherein the period between measurements is selected independently of the period between measurements of the first indicator;
    b) comparing the measurement of the second indicator with the second predetermined threshold; and
    c) issuing a third RRT signal in the event the second measurement is equal to or beyond the second predetermined threshold.

8. The method of claim 7, further comprising confirming that the measurement of the second indicator is equal to or beyond the second predetermined threshold prior to issuing the second or third RRT signal.

9. The method of claim 8, further comprising resetting the status register to zero, in the event the measurement of the second indicator is not equal to nor beyond the-predetermined second threshold.

10. The method of claim 8, wherein the first indicator of battery strength is battery terminal voltage.

11. The method of claim 10, wherein the battery is a 3-volt per cell silver vanadium oxide (SVO) battery and the predetermined first threshold is 2.35-volts per cell.

12. The method of claim 11, wherein the intermediate threshold is 2.45-volts per cell.

13. The method of claim 11, wherein the second indicator of battery strength is capacitor charge time.

14. The method of claim 13, wherein the capacitor has a total capacitance of about 5 to 20 $\mu F$ and the second predetermined threshold is 15 seconds.

15. The method of claim 14, wherein confirming the capacitor charge time comprises dumping the capacitor's charge and recharging the capacitor while measuring the capacitor charge time for a second time.

* * * * *